United States Patent [19]

McManus

[11] Patent Number: 5,245,069
[45] Date of Patent: Sep. 14, 1993

[54] PROCESS FOR THE PREPARATION OF BIS(ARYL)-PHOSPHOROHALIDATES

[75] Inventor: James W. McManus, Leesburg, Ga.

[73] Assignee: Merck & Co., Inc., Rahway, N.J.

[21] Appl. No.: 966,786

[22] Filed: Oct. 27, 1992

[51] Int. Cl.$^5$ .............................................. C07F 9/14
[52] U.S. Cl. ...................................... 558/148; 558/101
[58] Field of Search ................................. 558/101, 148

[56] References Cited

U.S. PATENT DOCUMENTS 3,689,602  9/1972  Ismail ..................................... 558/85
3,772,414  11/1973  Baker et al. ........................... 558/101
3,965,220  6/1976  Schumacher .......................... 558/101
4,845,261  7/1989  Fuentes ................................. 558/101

*Primary Examiner*—Mary C. Lee
*Assistant Examiner*—Michael G. Ambrose
*Attorney, Agent, or Firm*—Mark R. Daniel; Joseph F. DiPrima

[57] ABSTRACT

This invention relates to a novel process for preparing bis(aryl)phosphorohalidates which are useful in the synthesis of various enol phosphates. The process of this invention provides a means of producing a high-yield, high-purity product without the need for costly crystallization or impractical, high temperature distillations.

8 Claims, No Drawings

PROCESS FOR THE PREPARATION OF BIS(ARYL)-PHOSPHOROHALIDATES

BACKGROUND OF THE INVENTION

The present invention relates to a novel process for preparing bis(aryl)phosphorohalidates. In particular, this invention relates to a process for preparing bis(2,4-dichlorophenyl)phosphorochloridate, a compound which is required for the synthesis of an enol phosphate intermediate in the manufacture of certain carbapenem antibiotics.

Various processes for the manufacture of bis(aryl)-phosphorohalidates have been disclosed in the art. For example, U.S. Pat. No. 4,845,261, which is incorporated herein by reference, discloses a process for preparing bis(2,4-dichlorophenyl)phosphorochloridates wherein the arylphosphorohalidates are produced in one-step procedure performed within a single temperature range utilizing dialkylaminopyridines. Unlike the process of the present invention, U.S. Pat. No. 4,845,261 provides no means of isolating and recovering the valuable phophorodihalidate (monoester) intermediate, and requires an extensive product isolation via crystallization from an organic solvent.

U.S. Pat. No. 3,965,220 discloses a process in which aromatic alcohols and phosphorus halides are allowed to react in the presence of amine catalysts to form various esters of phosphorus acids, including phosphorochloridate estes. Unlike the process of the present invention, however, the process of U.S. Pat. No. 3,965,220 involves a two-stage procedure in which monoesters are formed initially at 85°–135° (preferably 105°) and diesters are then formed, after addition of more phenol, at 130°–165° (preferably 150°). Although the claims of the U.S. Pat. No. 3,965,220 give a temperature range of 85°–165° for preparing "a mono or diester," the specification discloses methods that describe only the range of 85°–135° for monoesters and 130°–165° for diesters.

The process of U.S. Pat. No. 3,965,220 is suitable for the preparation of dihalidates (monoesters) in high yield. However, when bis(aryl)phosphorohalidates are the target, a high temperature, high vacuum distillation is required to separate the desired product from decomposition products and catalysts. Such high temperature distillations frequently result in significant disproportionation and are generally impractical and uneconomical on a commercial scale.

U.S. Pat. No. 3,772,414 discloses a process similar to that of U.S. Pat. No. 3,965,220, except that various ureas instead of an amine are used as catalysts. In U.S. Pat. No. 3,772,414, as in U.S. Pat. No. 3,965,220, an impractical high-temperature distillation is required to purify any diesters.

U.S. Pat. No. 3,689,602 discloses a process in which 2,4-dichlorophenol and phosphorous oxychloride are allowed to react in the presence of heteroaromatic amines such as pyridine. Product isolation in U.S. Pat. No. 3,689,602 is limited to crystallization from organic solvents.

It has been surprisingly discovered that the labor intensive crystallization technique utilized in the art can be supplanted by an efficient, high-vacuum, wiped-film evaporator purification in which the dichloride intermediate is retrieved as the distillate with the desired product being recovered in a semipure form as the evaporator bottoms.

It is, therefore, an object of the present invention to provide a novel process for the preparation of bis(aryl)-phosphorohalidates which provide a means for producing a high-purity product without the need for costly crystallization or impractical high temperature distillation processes previously known in the art. It is also an object of this invention to provide an improved process for the preparation of bis(aryl)phosphorohalidates in higher yields than processes previously known in the art. It is further an object of this invention to provide a process for the preparation of bis(aryl)phosphorohalidate which eliminates air emissions and organic waste.

SUMMARY OF THE INVENTION

The present invention provides a process for the preparation of a compound having the formula I:

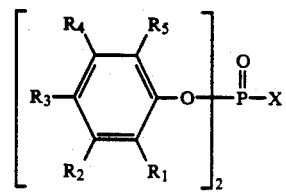

wherein:
$R_1$, $R_2$, $R_3$, $R_4$ and $R_5$ are hydrogen, $C_1$–$C_6$ alkyl, $C_1$–$C_6$ alkoxy, nitro or a halogen; and
X is bromine or chlorine;
comprising a novel combination of catalyst level, reaction temperature, reagent charge and a high vacuum, wiped-film evaporator purification in which the dichloridate intermediate is retrieved as the distillate with the desired product being recovered in a semipure form as the evaporator bottoms.

DETAILED DESCRIPTION OF THE INVENTION

The present invention provides a novel process for the preparation of a compound having the formula I:

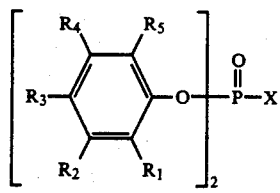

wherein:
$R_1$, $R_2$, $R_3$, $R_4$ and $R_5$ are hydrogen, $C_1$–$C_6$ alkyl, $C_1$–$C_6$ alkoxy, nitro or a halogen; and
X is bromine or chlorine; comprising the steps of:
a) reacting a phosphoryl halide of the formula $POX_3$, wherein X is defined as above, with a one to two-fold molar quantity of a phenol of the formula R—OH, wherein R is defined as above, in the presence of a dialkylaminopyridine and an arylphosphorodihalidate under a nitrogen atmosphere;
b) heating the reaction mixture at a temperature of from about 110° C. to about 140° C. for such period of time until the phenol has been consumed;

c) cooling the reaction mixture to about 15° C. to about 30° C. for such period of time to effect crystallization of the catalyst;

d) removing the catalyst by filtration;

e) collecting the filtrate, containing the bis(aryl)phosphorohalidate, arylphosphorodihalidate, and the arylphosphate;

f) passing the filtrate through a wiped-film evaporator under high vacuum conditions to distill the arylphosphorodihalidate; and g) collecting the bis(aryl)phosphorohalidate product which distributes in the evaporation bottoms.

The term halogen includes fluorine, chlorine, bromine, and iodine.

The term "$C_1-C_6$ alkyl" refers to straight or branched chain aliphatic hydrocarbon groups having 1 to 6 carbon atoms, also referred to as lower alkyl. Examples of $C_1-C_6$ alkyl include methyl, ethyl, propyl, butyl, pentyl, hexyl, and the isomeric forms thereof.

The term "$C_1-C_6$ alkoxy" refers to straight or branched chain alkyl groups having 1 to 6 carbon atoms. Examples of $C_1-C_6$ alkoxy are methoxy, ethoxy, propoxy, butoxy, pentoxy, hexoxy, and the isomeric forms thereof.

The term "period of time" represents a length of time sufficiently long to consume the maximum amount of starting materials, but sufficiently short to allow only a minimum amount of the starting materials, intermediates or product to decompose. The term includes a length time of about 10 hours to about 24 hours. A preferred period of time is a time length of about 15 hours to about 20 hours.

The following scheme illustrates a reaction sequence in which the process of the instant invention is employed.

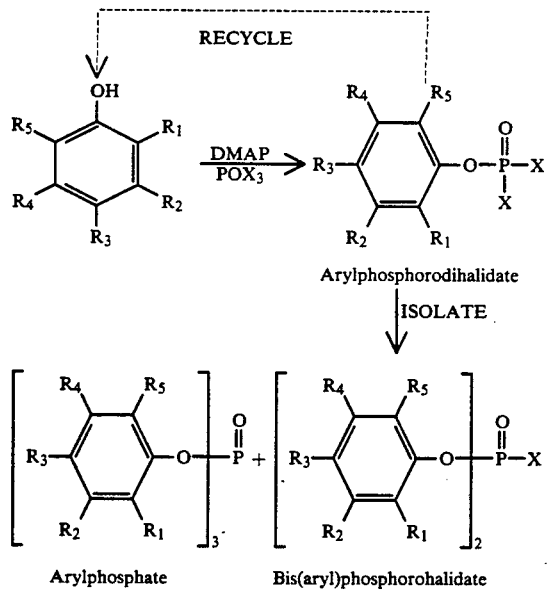

wherein:

$R_1$, $R_2$, $R_3$, $R_4$ and $R_5$ are hydrogen, $C_1-C_6$ alkyl, $C_1-C_6$ alkoxy, nitro, or a halogen; and X is bromine or chlorine.

The phosphoryl halide (from 0.5 moles to 1 mole halide per mole of phenol), a catalytic amount (2 to 3 mole % of phenol) of 4-(N,N-dimethylamino) pyridine or 4 pyrrolidinopyridine, and an appropriate quantity of dihalidate intermediate, recycled from a previous batch, are first combined under a nitrogen atmosphere.

The mixture is then heated to about 110° C. to about 140° C. and aged until all the phenol has been consumed. The mixture is cooled to about 15° C. to 30° C. and aged for several hours to effect crystallization of the catalyst as its hydrohalide salt. The catalyst is removed by filtration and may be recycled to a forthcoming batch without treatment.

The filtrate, containing the desired bis(aryl)phosphorohalidate, an intermediate arylphosphorodihalidate, and a small quantity of arylphosphate is then passed through a wiped-film evaporator under high vacuum conditions (0.5 to 5 mm Hg) to distill the phosphorodihalidate intermediate for recycle to a forthcoming batch.

The desired bis(aryl)phosphorohalidate product then distributes in the evaporation bottoms at a yield of 90% to 95%.

The reaction scheme incorporates a critical combination of catalyst level, reaction temperature, reagent charge, and most importantly, optimum recycle of a crucial dichloridate intermediate. The purification differs from the labor intensive crystallization technique utilized in the prior art and is supplanted by an efficient, high-vacuum, wiped-film evaporator purification in which the dichloridate intermediate is retrieved as the distillate with the desired product being recovered in a semipure form as the evaporator bottoms.

The novel process of this invention exhibits many additional advantages over the prior art processes. In the present invention, the processing efficiency (production level for a given time period) is enhanced by more than 400% over prior art processes due to a significantly higher yield as well as higher product volume resulting from solvent-free processing. Moreover, since no organic solvents are required at any point in the process, air emissions are non-existent. The present invention provides no organic waste since both the catalyst and the intermediate arylphosphorodihalidate are recycled and the bis(aryl)-phosphorohalidate distributes in the wiped-film evaporator bottoms in such high purity that no further treatment is required. The novel process of this invention is also safer to operate since the static charge buildup inherent in the prior art crystallization process is non-existent. Finally, the process of this invention makes it much easier to exclude moisture from the process, thus allowing the water-reactive product to have a significantly longer shelf-life.

The rationale behind the improvements of the novel process of this invention is best understood by comparing the synthetic strategy of the process of this invention with that of the prior art processes in view of general phosphorous chloride chemistry.

Initially, phosphoryl chloride (1), with its three equivalent chlorine atoms, may be successively substituted with a phenol (2) as shown in Eq. 1, leading to compounds (3), (4) and (5).

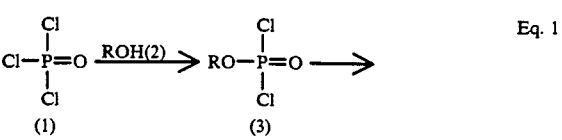

-continued

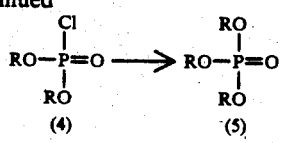
(4) (5)

With each additional substitution, the phosphorous atom becomes less electrophilic due to a conjugation effect (6),

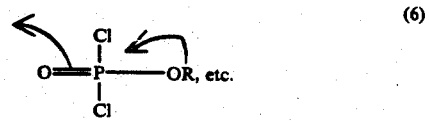
(6)

thus requiring more vigorous conditions to effect higher yield at each addition. Although the phosphorous chlorides follow the reactivity sequence (1)<(3)<(4), the differences in reactivity are not sufficient that either (3), an intermediate, or (4), the desired product, can be made exclusively.

The prior art process reaction conditions were selected to produce the maximum amount of the targeted chloridate (4) in one stage. With this approach the product distribution is dictated exclusively by the relative reactivities of the three aforementioned compounds, leading to a maximum yield to chloridate of 70-75% with the remaining 25-30% being approximately equal quantities of dichloridate (3) and overreaction product, phosphate (5). In the subsequent purification, the desired chloridate as well as the innocuous phosphate, both of which are solids, are cocrystallized from cold hexane, leaving most of the liquid dichloridate in solution. The semipure product is isolated by centrifugation, then reslurried in hexane to insure complete removal of the dichloridate. The product is again centrifuged, then dried under vacuum and drummed in an overall yield of approximately 60%.

The process is complicated, requiring a number of unit operations, large quantities of solvent, significant labor, and an inordinate amount of equipment. Moreover, the cold temperatures and the additional handling required for the isolation make it particularly difficult to completely exclude moisture from the highly water-reactive chemicals of the process. In fact, water contamination, even at very low levels, has historically limited product shelf-life to less than three months, even at sub-zero storage temperatures, significantly increasing the overall manufacturing cost.

The stategy of the novel process of this invention, is basically to produce as much chloridate as possible while minimizing the formation of phosphate, an irreversibly produced compound. The yield is then enhanced by isolating and recycling the intermediate dichloridate. Phosphate formation is first limited by making the following modifications: reducing the phenol/phosphoryl chloride charge ratio from 1.85 to 1.4, reducing the reaction temperature from 140° C. to 120° C., reducing the catalyst level from 3 mol % of the phenol to 2.25 mol %, and increasing the reaction time from eight hours to seventeen. Under these conditions a chloridate/dichloridate/phosphate product ratio is typically 55/43/2. Following the reaction, the intermediate dichloridate is isolated by distillation from the reaction mixture via a wiped-film evaporator at approximately 95° C. and 0.5 mm Hg (jacket temperature on the WFE actually set at 140° C.) and is then recycled to the forthcoming batch. The desired chloridate product, along with any phosphate produced, distributes in the evaporator bottoms and is drummed as a heavy oil which later solidifies.

The reaction conditions of the novel process of this invention afford product in the highest yield (Ca. 90%, based upon phenol) and purity (84-88%) at the lowest manufacturing cost. As one increases the dicloridate recycle approaching steady-state, phosphate formation, which has a negative impact on yield, increases. This is due simply to an increase in competition between the dichloridate and phosphoryl chloride for the starting phenol. Clearly then, one could reduce the phosphate formation by further decreasing the initial phenol/phosphoryl chloride change ratio. The price in taking this approach, however, is a reduction in chloride throughout. It is more advantageous to settle for a higher production rate than to take a meager increase in yield. The reaction conditions thus suggested afford product in the highest yield (ca. 90%, based upon phenol) and purity (84-88%) at the lowest manufacturing cost.

The phosphorylation reactions involved in the process of this invention are promoted by suitable dialkylaminopryidines. For the purposes of this invention, the term "dialkylaminopyridine" includes pyridine substituted at the 2- or 4-position (preferably the 4-position) with an N,N-di($C_1$-$C_6$ alkyl)amino group; an N,N-di($C_4$-$C_7$ cycloalkyl)-amino group; an N-($C_1$-$C_6$ alkyl)-N-($C_4$-$C_7$ cycloalkyl)amino group; or a 1-azacycloalkyl group having from 4 to 7 ring nucleus atoms, the 1-azacycloalkyl group being optionally substituted at one or more ring carbon atoms by $C_1$-$C_6$ alkyl. Examples of N,N-di($C_1$-$C_6$ alkyl)amino include N,N-dimethylamino, N,N-diethylamino, N-ethyl-N-methylamino, and the like. Examples of N,N-di-($C_4$-$C_7$ cycloalkyl)amino include N,N-dicyclopentylamino, N,N-dicyclohexylamino, N-cyclohexyl-N-cyclopentylamino, N,N-dicyclohexylamino, N-cyclohexyl-N-cyclopentylamino, and the like. Examples of N-($C_1$-$C_6$ alkyl)-N-($C_4$-$C_7$ cycloalkyl)amino include N-cyclopentyl-N-methylamino, N-cyclohexyl-N-methylamino, N-cyclohexyl-N-ethylamino, and the like. Examples of 1-azacycloalkyl include 1-pyrrolidinyl, 1-piperidinyl, and the like, and optionally alkyl- substituted derivatives thereof, such as 4-methyl-1-piperidinyl and the like. A preferred dialkylaminopyridine is 4-dimethylaminopyridine.

A dialkylaminopyridine need not be present in a stoichiometric amount but instead may be present in a catalytic amount, typically in the range of 1 to 10 molar percent relative to the phosphorus oxyhalide. Moreover, hydrohalide salts of dialkylaminopyridines are essentially equally effective at prompting the reaction. Preferred dialkylaminopyridine salts include 4-dimethylaminopyridine hydrochloride and hydrobromide. Where a salt of a dialkylaminopyridine or only a catalytic amount of a dialkylaminopyridine is used, the hydrogen halide produced in the reaction is typically allowed to escape the reaction mixture as a gas that, if desired, can be trapped, for example, in a scrubber.

Various chemical and physical properties make 4-dimethylaminopyridine a particularly advantageous dialkylaminopyridine for the process of this invention. Chemical properties make 4-dimethylaminopyridine an exceptional catalyst for acylations when compared to pyridine or other amines. For a review of such properties, see Hofle, Steglich, and Vorbruggen, *Angew. Chem. Int. Ed. Engl.*, 17, 569–583 (1978). One might except similarly exceptional behavior for phosphorylations. See, for example, Hofle, Steglich, and Vorbruggen at p. 575. Certain physical properties of 4-dimethylaminopyridine and its hydrochloride salt also provide distinct advantages. Both the free amine and its hydrochloride salt are crystalline solids at ordinary temperatures. Moreover, the free amine is essentially non-hygroscopic and the hydrochloride salt seems less hygroscopic than is usual for amine hydrochlorides. Thus, 4-dimethylaminopyridine and its hydrochloride salt are easily manipulated, an advantage when working with the water-sensitive reactants used in the process of this invention. Where the process of this invention is performed without adding a separate solvent, 4-dimethylaminopyridine can be removed as the hydrohalide salt by adding a suitable crystallization solvent as described below. The salt can be essentially completely recovered and then recycled, a feature of the process having distinct advantages in a commercial application. For example, recovery and recycling of the salt permits optimization of the reaction with less concern for the economics of lost amine catalyst.

REACTION SCHEME

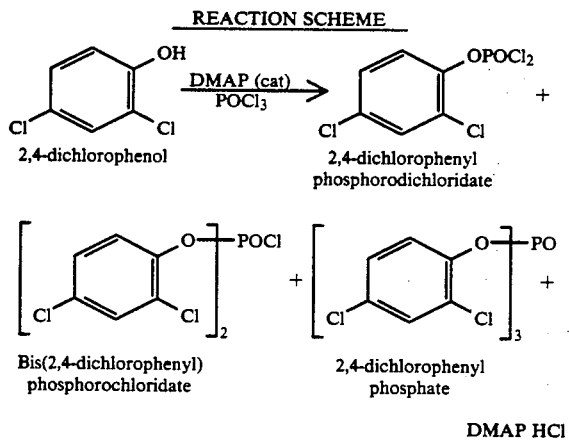

The preferred embodiment of this invention involves a process for preparing bis(2,4-dichlorophenylphosphorochloridate having the formula:

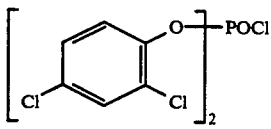

comprising the steps of:

a) reacting a phosphorylchloride with a one to two fold molar quantity of 2,4-dichlorophenol in the presence of 4-dimethylaminopyridine and 2,4-dichlorophenylphosphorodichloridate under a nitrogen atmosphere;

b) heating the reaction mixture at a temperature of from about 110° C. to about 140° C. for such period of time until the 2,4-dichlorphenol has been consumed;

c) cooling the reaction mixture to about 15° C. to about 30° C. for such period of time to effect crystallization of the catalyst;

d) removing the catalyst by filtration;

e) collecting the filtrate containing the bis(2,4-dichlorophenyl)phosphorochloridate, 2,4-dichlorophenylphosphorodichloridate and 2,4-dichlorophenylphosphate;

f) passing the filtrate through a wiped-film evaporator under high vacuum conditions to distill the 2,4-dichlorophenylphosphorodichloridate;

g) collecting the bis(2,4-dichlorophenyl)phosphorochloridate product which distributes in the evaporation bottoms.

EXAMPLES

Examples provided are intended to assist in a further understanding of the invention. Particular materials employed, species and conditions are intended to be further illustrative of the invention and not limitative of the reasonable scope thereof.

EXAMPLE 1

Method for Preparing (2,4-dichlorophenyl)phosphorochloridate

To a melt of 2,4-dichlorophenol (249.2 g, 1.53 mol) at approximately 60° C. was added 4-dimethylaminopyridine (4,21 g, 0.034 mol), followed by 2,4-dichlorophenylphosphorodichloridate (130.1 g, 0.46 mol) distilled from a previous batch, and finally phosphoryl chloride (116.6 g, 0.76 mol). The mixture was then heated under a slight positive pressure of nitrogen to 120° C. and aged under a nitrogen atmosphere at that temperature for seventeen hours. The mixture was then cooled to 20° C. where it was aged an additional seventeen hours in order to effect complete precipitation of the DMAP catalyst as the hydrochloride salt. The crude reaction mixture was then filtered under nitrogen through a course glass filter to remove the catalyst. The filtrate was then heated to 50° C. while slowly reducing the pressure to 10–15 mm Hg in order to ensure complete removal of residual HCl. The 2,4-dichlorophenylphosphorodichloridate intermediate is then recovered for recycle to the forthcoming batch by distillation in a single pass over a wiped-film evaporator at (80° to 95° C. and 0.5 to 1.0 mm Hg). The bis(2,4 dichlorophenyl)-phosphorochloridate product distributed in the evaporator bottoms in 90% yield. Purity by HPLC analysis was 90%. $^{31}$P NMR spectra of the still bottoms measured relative to $D_3PO_4$ at 0.00 ppm indicated the presence of 0.2% 2,4-dichlorophenylphosphorodichloridate at 2.1 ppm; 90% bis(2,4-dichlorophenyl)phosphorodichloridate at −6.9 ppm; 8% 2,4-dichlorophenylphosphate at −19.3 ppm; and 2% 2,4-dichlorophenyl pyrophosphate at −25.5 ppm.

EXAMPLE 2

Method for Preparing (2-chlorophenol)phosphorochloridate 2-chlorophenol (25.7 g, 0.2 mol), 2-chlorophenylphosphordichloridate (15.1 g, 0.06 mol), 4-dimethylaminopyridine (0.49 g, 0.004 mol), and phosphoryl chloride (15.12 g, 0.098 mol) were combined and treated as in Example 1.

Upon distillation (55° C. and 0.5 mmHg), ca. 14 g of 2-chlorophenylphosphorodichloridate was recovered. $^{31}$P NMR of the distillate showed a single component at δ=2.88 ppm relative to $D_3PO_4$ at 0.00 ppm.

The still bottoms were recovered in a bis (2-chlorophenyl) phosphorochloridate yield of 90%. $^{31}$P NMR analysis indicated 90% bis (2-chlorophenyl) phosphorochloridate at δ=6.67 ppm; 0.25% 2-chlorophenylphosphorochloridate at 2.88 ppm; 6.1% 2-chlorophenylphosphate at δ=19.5 ppm; 2.8% 2-chlorophenyl pyrophosphate at δ=27.46 ppm. Spectra were recorded relative to D₃PO₄ at δ 0.00 ppm.

| MATERIALS | |
|---|---|
| 2,4-dichlorophenol (Aldrich) MW = 163.0, KF = <0.001% | 249.2 g (1.53 mol) |
| Phosphoryl Chloride (Aldrich) MW = 153.33 | 116.6 g (0.76 mol) 70.9 mL |
| 2,4-Dichlorophenyl Phosphorodichloridate MW = 279.87 (recycled from previous batch) | 130.1 g (0.46 mol) |
| DMA (Aldrich) MW = 122.17 | 4.21 g (0.034 mol) |

Method for Preparing N-Formamidoylthienamycin

Step A

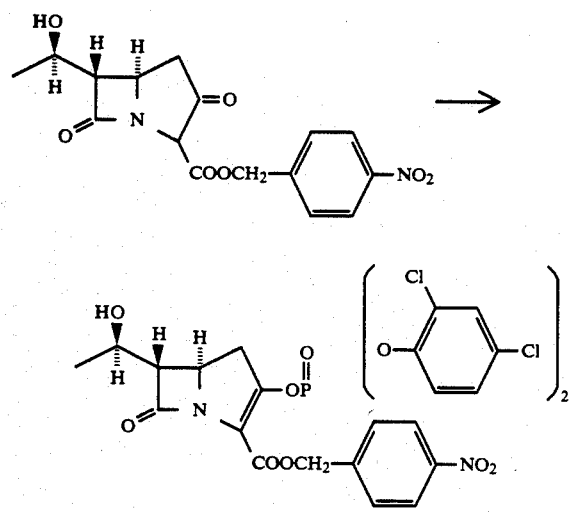

To a cooled (−50°) solution of p-nitrobenzyl (3R,5R,6S)-2-oxo-6-[(1R)-1-hydroxyethyl]carbapenem-3-carboxylate (1.964 g, 5.64 mmoles) in N-ethylpyrrolidinone (24.11 g) was added diisopropylethylamine (1.75 g, 13.5 mmoles) in one portion followed by bis(2,4-dichlorophenyl) phosphorochloridate as a melt over a 30 minute period (2.45 g, 6.03 mmole; see Example 1). The mixture was stirred for two hours and used in the next step without isolation of the enol phosphate intermediate.

Step B

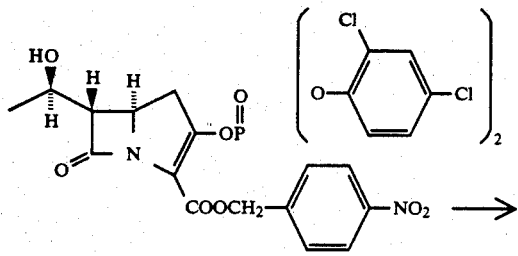

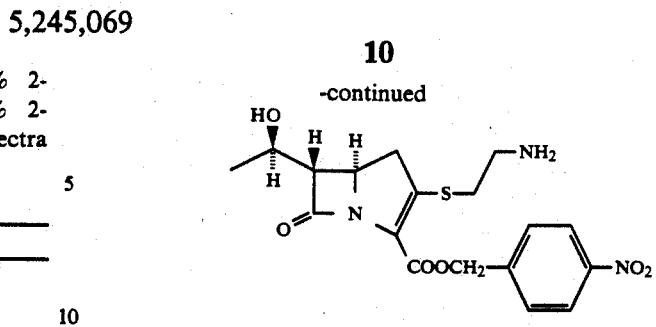

The reaction mixture from Step A was cooled to −62°. A solution of cysteamine hydrochloride (0.70 g, 6.16 mmoles) in N-ethylpyrrolidinone (2 ml) was added over a five-minute period, during which time the temperature was maintained below −60°. The reaction was stirred at −60° for 1.5 hours and used in the next step without isolation of the aminoethythio intermediate.

Step C

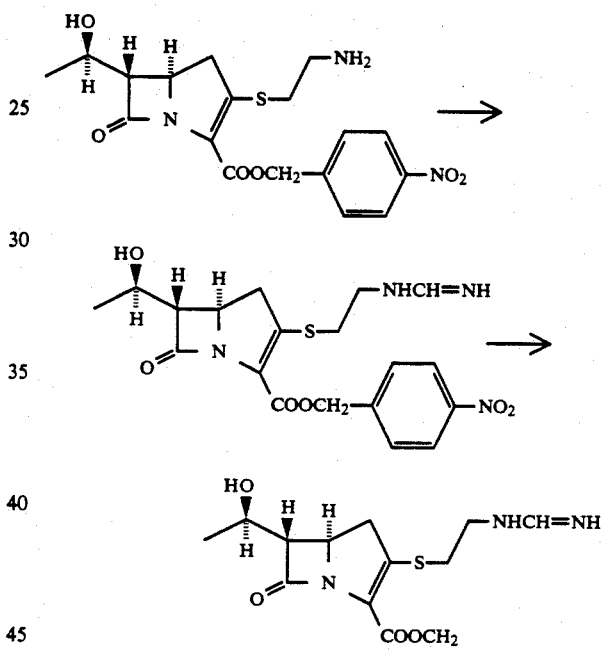

Amidine formation and hydrogenolysis of the ester group were performed using the general method described in U.S. Pat. No. 4,292,436, modified as described herein, to give the title compound in 82% yield (as determined by HPLC) in aqueous solution. A reaction mixture prepared as in Step B was maintained at a temperature of about −50°. Diisopropylethylamine (1.06 g, 8.21 mmole) was added, followed by benzyl formimidate (1.09 g, 6.35 mmole). The mixture was stirred vigorously for 20 minutes at −50°, after which HPLC indicated residual unreacted aminoethylthio intermediate. Additional benzyl formimidate (0.05 g) was added and the mixture was warmed to −20° over fifteen-minute period and held at −20° for 20 minutes. The reaction mixture was poured into a mixture of water (150 ml), butanol (120 ml), ethyl acetate (60 ml), and 0.5M N-methylmorpholine (60 ml) at 5° and pH 6.8. Hydrogenolysis of the mixture was performed in an unthermostatted autoclave at 15° (initial) to 23° (final) using hydrogen gas (100 psi) over 20% Pd(OH)₂ on carbon catalyst (0.9 g) for 1.5 hours. The mixture was filtered at 5° through a filter aid. The aqueous layer was separated and assayed for N-formamidoylthienamycin.

What is claimed is:

1. A process for preparing a compound having the formula I:

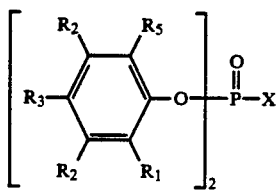

wherein:

$R_1$, $R_2$, $R_3$, $R_4$ and $R_5$ are hydrogen, $C_1$-$C_6$ alkyl, $C_1$-$C_6$ alkoxy, nitro or a halogen; and X is bromine or chlorine; comprising the steps of:

a) reacting a phosphoryl halide of the formula $POX_3$, wherein X is defined as above, with a one to two-fold molar quantity of a phenol of the formula,

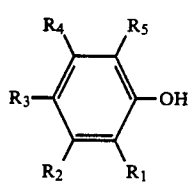

in the presence of a dialkylaminopyridine and an arylphosphorodihalidate

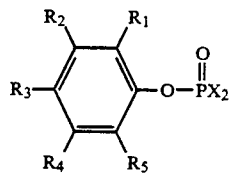

under a nitrogen atmosphere;

b) heating the reaction mixture at temperature of from about 110° C. to about 140° C. for such period of time until the phenol has been consumed;

c) cooling the reaction mixture to about 15° C. to about 30° C. for such period of time to effect crystallization of the catalyst;

d) removing the catalyst by filtration;

e) collecting the filtrate, containing the bis(aryl)-phosphorohalidate, an arylphosphorodihalidate, and the arylphosphate;

f) passing the filtrate through a wiped-film evaporator under high vacuum conditions to distill the arylphosphorodihalidate; and g) collecting the bis(aryl)phosphorohalidate product which distributes in the evaporation bottoms.

2. The process according to claim 1, wherein X is chlorine.

3. The process according to claim 1, wherein R is 2,4-dichlorophenyl.

4. The process according to claim 1, wherein dialkylaminopyridine is 4-(N,N-dimethylamino)pyridine.

5. The process according to claim 1, wherein bis-(aryl)phosphorohalidate is bis(2,4-dichlorophenyl)phosphorochloridate.

6. The process according to claim 1, wherein the phosphoryl halide is 2,4-dichlorophenol.

7. The process according to claim 1, wherein the arylphosphorodihalidate is 2,4-dichlorophenylphosphorodichloridate.

8. A process for preparing bis(2,4-dichlorophenyl-phosphorochloridate having the formula:

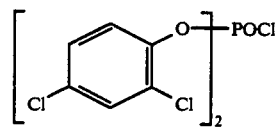

comprising the steps of:

a) reacting a phosphorylchloride with a one to two fold molar quantity of 2,4-dichlorophenol in the presence of 4-dimethylaminopyridine and 2,4-dichlorophenylphosphorodichloridate under a nitrogen atmosphere;

b) heating the reaction mixture at a temperature of from about 110° C. to about 140° C. for such period of time until the 2,4-dichlorphenol has been consumed;

c) cooling the reaction mixture to about 15° C. to about 30° C. for such period of time to effect crystallization of the catalyst;

d) removing the catalyst by filtration;

e) collecting the filtrate containing the bis(2,4-dichlorophenyl)phosphorochloridate, 2,4-dichlorophenylphosphorodichloridate and 2,4-dichlorophenylphosphate;

f) passing the filtrate through a wiped-film evaporator under high vacuum conditions to distill the 2,4-dichlorophenylphosphorodichloridate;

g) collecting the bis(2,4-dichlorophenyl)phosphorochloridate product which distributes in the evaporation bottoms.

* * * * *